United States Patent [19]

Klein et al.

[11] Patent Number: 5,070,025

[45] Date of Patent: Dec. 3, 1991

[54] PROCESS FOR THE DETERMINATION OF A PROTEIN ACCORDING TO FLUORESCENCE POLARIZATION IMMUNOASSAY PRINCIPLE

[75] Inventors: Christian Klein, Weilheim; Hans-Georg Batz, Tutzing; Ulrich Essig, Planegg; Kurt W. Naujoks, Penzberg, all of Fed. Rep. of Germany

[73] Assignee: Boehringer Mannheim GmbH, Mannheim, Fed. Rep. of Germany

[21] Appl. No.: 311,100

[22] Filed: Feb. 15, 1989

[30] Foreign Application Priority Data

Feb. 29, 1988 [DE] Fed. Rep. of Germany ....... 3806430

[51] Int. Cl.$^5$ .......................................... G01N 33/533
[52] U.S. Cl. .................................... 436/546; 435/7.1; 436/512; 436/536; 436/547
[58] Field of Search ................ 435/7.1; 436/536, 546, 436/547

[56] References Cited

U.S. PATENT DOCUMENTS 4,681,859  7/1987  Kramer .............................. 436/501

FOREIGN PATENT DOCUMENTS 0210410  4/1987  European Pat. Off. .

OTHER PUBLICATIONS

Schroer et al., Eur. J. Immunol. 13: 693-700 (1983).
Harper, H. et al., 1979, Chapter 34, Hormones. In: Review of Physiological Chem. Lange Medical Publications, Los Altos, Calif., pp. 519-520.

Primary Examiner—Sam Rosen
Attorney, Agent, or Firm—Felfe & Lynch

[57] ABSTRACT

The present invention provides a process for the determination of a protein according to the fluorescence polarization immunoassay principle in a homogeneous system by simultaneous incubation of the sample solution with a) a peptide sequence, labelled with a fluorescing compound, of 6 to 14 amino acids, two of which are cysteine which form a disulphide bridge with one another, the sequence thereby corresponding to an epitope sequence of the protein to be determined, and b) an antibody which is specifically bindable not only with the protein but also with the peptide sequence and displays for the fluorescing peptide sequence of the protein and the native protein molar relative affinities which differ by a factor of at most 6, and measurement of the depolarization of polarized light passed through the incubated solution.

8 Claims, 1 Drawing Sheet

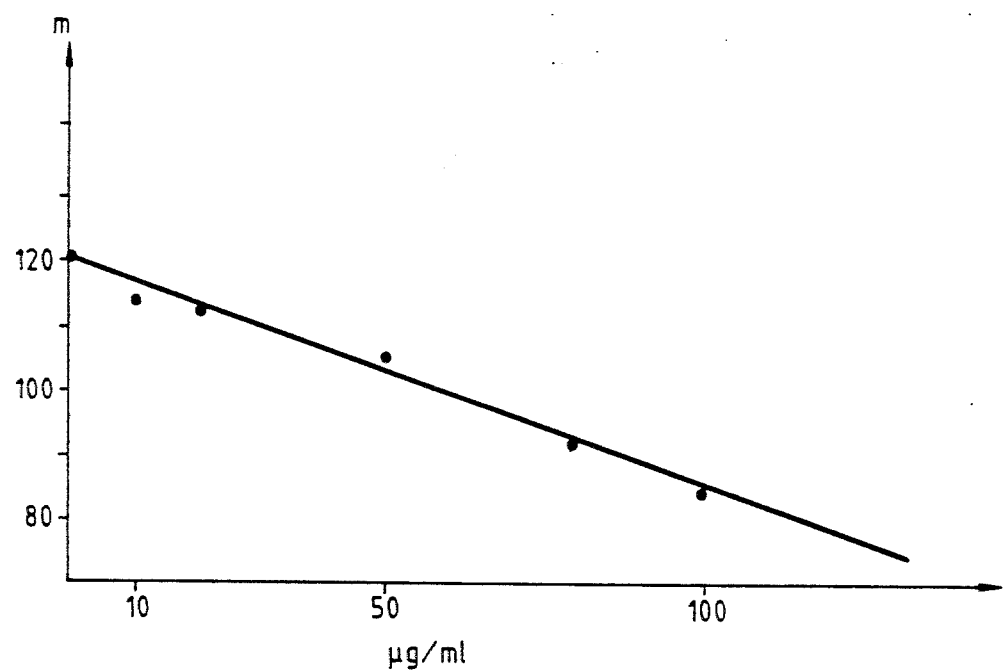

PROCESS FOR THE DETERMINATION OF A PROTEIN ACCORDING TO FLUORESCENCE POLARIZATION IMMUNOASSAY PRINCIPLE

The present invention is concerned with a process for the determination of a protein according to the fluorescence polarization immunoassay principle.

In the field of diagnosis and especially in the clinical field, in the last two decades, starting from processes according to the radio-immune assay principle, new variants of this method of detection have been continuously developed which permit ever more exact and specific determinations of specifically bindable substances.

The fluorescence polarization immunoassay has been developed as a very sensitive method of detection. This method depends upon the fact that a conjugate of a fluorescing substance and a small molecule, for example a hapten, moves very quickly in solution so that polarized light which is passed through the solution and excites the fluorescing substance is depolarized in the case of the emission due to the rotation of the conjugate taking place between impingement and emission. The degree of depolarization is thereby inversely proportional to the rate of rotation of the molecule.

In the case of binding the fluorescing substance to a large molecule, for example in the case of binding of a fluorescent-labelled hapten to the corresponding antibody, the movement of the whole conjugate is so very considerably limited that the polarized light is now no longer depolarized from the point of time when it impinges up to the point of time when it is emitted but rather again emerges polarized from the solution.

The depolarization can be determined with known devices. This behavior is now utilized for a detection process. For this purpose, into a solution which contains the specifically bindable component to be determined, there is added a conjugate of the component to be determined with a fluorescing substance, as well as an antibody which is bindable with both of them, i.e. not only the substance to be detected but also the fluorescence-labelled molecule, and the decrease of the depolarization is measured. The binding component present in the solution and the fluorescing molecule compete for the antibody. The amount of bound fluorescence-labelled substance can then be determined by the decrease of the polarization and is a measure of the amount of substance to be determined in the solution.

Important for this process is the differing mobility of the labelled binding component and of the conjugate of the labelled binding component and antibody. This only occurs when the binding component is very small. Therefore, this process can be carried out very well with haptens and provides good results. However, if large molecules are to be determined, then the differences in the size between labelled molecule and conjugate of labelled molecule and antibody are no longer sufficient to determine the decrease of the depolarization with sufficient accuracy. Therefore, this sensitive detection process could hitherto not be used for larger molecules.

Therefore, it is an object of the present invention to provide a process by which larger molecules can be sensitively detected in solutions.

Thus, according to the present invention, there is provided a process for the determination of a protein according to the fluorescence polarization immunoassay principle in a homogeneous system by simultaneous incubation of the sample solution with a) a peptide sequence, labelled with a fluorescing compound, of 6 to 14 amino acids, two of which are cysteine which form a disulphide bridge with one another, the sequence thereby corresponding to an epitope sequence of the protein to be determined, and b) an antibody which is specifically bindable not only with the protein but also with the peptide sequence and displays molar relative affinities for the fluorescing peptide sequence of the protein and for the native protein which differ at most by a factor of 6, and measurement of the depolarization of polarized light passed through the incubated solution.

With the components used according to the present invention, i.e. with fluorescing compound-labelled peptide and antibody, it is possible to detect large molecules in solution, this detection being very sensitive. The peptide sequences used according to the present invention can, when bound to a carrier protein, also be used simultaneously for the immunization, i.e. for the production of the antibodies required.

The process according to the present invention serves for the determination of proteins, especially in body fluids. The proteins to be determined are immunogenically active and can, therefore, also be referred to as antigens. The process can be used, for example, for the detection of hormones, enzymes and other biologically-active high molecular weight substances. When they are injected into an appropriate organism, these substances produce an immune reaction and lead to the formation of antibodies. The whole molecule is not immunogenically active but only certain regions, which are called epitopes. As a rule, these are comparatively small regions which include up to 10 amino acids and lie on the surface of the molecule. Proteins have many such epitopes on their surface so that, in the case of the immunization therewith, a plurality of different antibodies are produced which are directed against the individual epitopes. Furthermore, the individual antibodies differ with regard to their molar affinity to the antigen. In order to detect high molecular weight proteins which do not give any analytically evaluatable difference in depolarization of impinging and emitted light in a fluorescence polarization immunoassay, this invention uses a conjugate of a fluorescing compound and a peptide where the peptide amino acid sequence corresponds to the amino acid sequence of an epitope of the protein to be determined as epitope sequence, a sequence of 6 to 14 amino acids, two of which are cysteine, which form a disulphide bridge are used. If the epitope sequence of the protein to be determined contains more than two cysteines, then in the fluorescence-labelled peptide all cysteines except two are replaced by another amino acid, preferably alanine, in order to obtain a definite disulphide bridge. If the sequence contains more than two cysteines, then a mixture results of molecules which have disulphide bridges at different positions. In this case, there can be difficulties in the recognition of the molecule by the antibodies.

The peptide is produced in known manner. Processes for the synthesis of peptides are generally known and do not need to be explained here in more detail.

The peptide sequence is labelled with a fluorescing substance. As fluorescing compounds, there can be used compounds which have short fluorescence half lives, i.e. after excitation, the substance emits the energy very quickly in the form of fluorescence and again returns to the initial state. As fluorescing substances, there can be used, for example, fluorescein and the derivatives thereof, as well as resorufin, the use of resorufin being especially preferred.

The fluorescing substance is bound in known manner to the peptide sequence. The binding can take place either directly between the two components or via a spacer. The nature of the binding depends upon the fluorescing substance used and upon the peptide employed. Processes for this purpose are well known.

The binding of the fluorescing substance to the peptide must take place in such a way that the fluorescing substance does not disturb the epitope function of the peptide. Therefore, the binding preferably takes place on one of the chain ends of the peptide.

Furthermore, for the process according to the present invention, an antibody is used which is specifically bindable with the protein to be determined and also with the fluorescence-labelled peptide. In order to achieve precise results, it must show molar relative affinities for the fluorescence-labelled peptide sequence and for the native protein which differ at most by a factor of 6. The molar relative affinities are determined by a known microtiter ELISA. For this purpose, microtiter plates coated with the native protein are simultaneously incubated in each case with the antibody and the substance to be measured (native protein, fluorescence-labelled peptide) in several dilution series. The substance to be measured inhibits the binding of the antibody to the wall-bound antigen depending upon the affinity of the antibody to the substance and depending upon the concentration of the substance to be measured.

The binding of the antibody is determined by incubation with an anti-antibody-enzyme conjugate, for example, in the case of specificity investigations of monoclonal mouse antibodies, with a polyclonal antimouse Fc-sheep antibody-peroxidase conjugate. The binding is made visible by incubation with an appropriate enzyme substrate.

The concentration in mole/liter of the analyte to be measured associated with the half-maximum binding is designated as the molar relative affinity. The poorer the antibody binds the substrate to be measured, the higher is the value of the molar relative affinity.

The amount of antibody to be used is determined in a preliminary experiment. Microtiter plates coated with the native protein are incubated analogously with the antibody alone in various concentrations and the binding measured analogously. For the above-described measurement of the molar relative affinity, there is used the concentration of the antibody at which the half-maximum binding is observed.

Appropriate antibodies can be obtained, for example, by immunizing a suitable organism with the protein to be determined as immunogen and then an antibody is selected according to its binding strength for the fluorescence-labelled peptide. Such an antibody can also be obtained by immunizing a suitable organism with the peptide sequence as immunogen and then the antibody is selected according to its relative affinity for the native protein.

The selection takes place either by immunosorption when it is a polyclonal antibody or by screening when it is a monoclonal antibody.

Both types of antibodies can be used for the process according to the present invention. However, it is preferred to use monoclonal antibodies. Since, in the case of the process according to the present invention, only a single kind of antibody is used, it is important that the antibody is highly specific for the desired epitope and shows practically no cross-reactivities with other endogenic substances.

For the determination of a protein according to the present invention, a sample solution is incubated simultaneously with the fluorescence-labelled peptide and an antibody which is specifically bindable for the protein to be determined and the fluorescence-labelled peptide. The change of the depolarization of polarized light passed through the solution is measured. This change is a measure for the proportion of bound fluorescence-labelled peptide. From the amount of fluorescence-labelled peptide, which can be calculated by comparison with a standard curve, there is then calculated in known manner the amount of the protein to be determined in the solution.

The present invention also provides hybridoma cell lines 2E6 and 3C4, which were deposited on the Feb. 25, 1988, according to the Budapest Convention, at the European Collection of Animal Cell Cultures (ECACC), Great Britain. They have been given the deposit numbers 2E6 (ECACC 88022502) and 3C4 (88022501). From these cell lines one obtains monoclonal antibodies which react very specifically with the A-loop epitope of human insulin, as well as with a fluorescence-labelled sequence of this epitope. These antibodies can be used for the determination of insulin in a fluorescence polarization determination process.

Thus, according to the present invention, a process is provided with which it is possible to detect proteins very specifically and very sensitively. Furthermore, there are provided monoclonal antibodies which are suitable for the process.

The following Examples are given for the purpose of illustrating the present invention, with reference to the accompanying drawing, the Figure of which shows a calibration curve.

EXAMPLE 1

A peptide amino acid sequence was synthesized which corresponds to the human insulin A-chain loop. The solid phase synthesis was carried out in a semi-automatic peptide synthesizer of the firm Labortech, Bubendorf, Switzerland. As N-amino protective group, there was used the FMOC ((9-fluorenyl)-methoxycarbonyl) radical.

A description of this peptide synthesis method is given by J. Meienhofer et al., Int. J. Peptide Protein Res., 13, 35–42/1979. As described by Meienhofer, the C-terminal FMOC-amino acid was coupled to p-alkoxybenzyl alcohol resin (Bachem, Bubendorf, Switzerland).

Synthesis protocol for a synthesis cycle:

| step | time | reagent/solvent |
| --- | --- | --- |
| 1 | 2 × 1 min. | dimethylformamide (DMF) |
| 2 | 1 × 3 min. | piperidine/DMF (1:4 v/v) |
| 3 | 1 × 7 min. | piperidine/DMF (1:4 v.v) |
| 4 | 4 × 0.5 min. | DMF |
| 5 | 2 × 0.5 min. | isopropanol |
| 6 | stop | ninhydrin test |
| 7 | 2 × 1 min. | DMF |
| 8 | stop | addition of the next Fmoc-amino acid and 1-hydroxybenzotriazole (HOBt) in DMF |
| 9 | 2 min. | shaking |
| 10 | stop | addition of dicyclohexylcarbodiimide (DCC) in dichloromethane (DCM) |

| step | time | reagent/solvent |
|---|---|---|
| 11 | 90 min. | coupling |
| 12 | 3 × 1 min. | DMF |
| 13 | 2 × 1 min. | isopropanol |
| 14 | stop | ninhydrin test |

As volumes of the washing and coupling steps, there were, in each case, used 15 times the weight of the starting resin. The ninhydrin test was carried out as described by E. Kaiser et al. in Anal. Biochem., 34, 595-598/1970. If, in step 14, the ninhydrin test indicated still free amino groups, then the protocol was repeated from step 8. For the coupling according to steps 8 to 11, the Fmoc-amino acid and DCC were each used in threefold molar amount, referred to the loading of the starting resin. HOBt was used in the 4.5 fold molar amount.

After the coupling of the last N-terminal Fmoc-amino acid, steps 1 to 5 of the synthesis cycle were followed in order to split off the Fmoc protective group. Thereafter, the resin was shaken in a 15 fold volume of dichloromethane (DCM)/trifluoroacetic acid (TFA) (1:1 v/v) for 2 hours at ambient temperature. After filtering, the resin was further washed twice with dichloromethane/trifluoroacetic acid (4:1 v/v) and all the filtrates were combined and evaporated in a vacuum, with the addition of toluene, at 25° C. The residue was mixed with diethyl ether and the solid material was filtered off and dried.

According to the above-described scheme, there was synthesized the A-chain loop

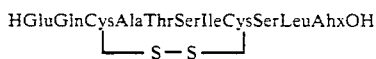

As starting resin, there was used 5 g. Fmoc Ahx (ε-amino-hexanoic acid-p-alkoxybenzyl alcohol) resin, loaded with 0.45 mMole/g. In the synthesis cycles, the following Fmoc-amino acids were used successively:

1. 2.39 g. Fmoc Leu
2. 2.59 g. Fmoc Ser (tBu)
3. 3.95 g. Fmoc Cys (Trt)
4. 2.39 g. Fmoc Ile
5. 2.59 g. Fmoc Ser (tBu)
6. 2.68 g. Fmoc Thr (tBu)
7. 2.10 g. Fmoc Ala
8. 3.95 g. Fmoc Cys (Trt)
these couplings were, in
9. 2.49 g. Fmoc Gln
each case, repeated once
10. 3.13 g. Fmoc Glu (OtBu)

tBu: t-butyl ether
Trt: trityl
OtBu: t-butyl ester

Before splitting off the peptide from the resin, the protective groups of the cysteines were split off and the cysteines cyclized to form a disulphide bridge: a mixture of 15 ml. hexafluoroisopropanol and 46 ml. DCM was mixed with iodine until saturated and excess iodine was filtered off through a fluted filter. There was added thereto 500 mg. of the above-obtained peptide resin. The resulting mixture was shaken for 2 hours, filtered and washed, in each case three times, with DCM, DMF and isopropanol. Thereafter, the peptide was split off from the resin as described above. Yield: 120 mg. of crude product.

The crude product was chromatographed on Polygosil C 18 5μ, 250×20 mm. (Bischoff). Eluent A: water with 0.1% TFA, eluent B: 65% isopropanol in water with 0.1% TFA; 20 to 80% in 120 minutes. Flow rate: 3.5 ml./minute, detection at 226 nm. There were obtained 47 mg. of pure substance.

TLC: (silica gel, elution agent: n-butanol/glacial acetic acid/water 4:1:1 v/v/v)=$R_f$=0.44.

FAB-MS (fast-atom bombardment-MS) (positive) $MH^+$: 1165 (calc. 1165.5).

58 mg. of the peptide obtained were taken up in 15 ml. of water and the solution adjusted to pH 8.5 with a 5% aqueous solution of potassium carbonate. A solution of 21.5 mg. N-(resorufinylcarbonyl)-sarcosine-N'-hydroxysuccinimide ester in 15 ml. dioxan was added thereto. The preparation of this reagent is described in Federal Republic of Germany Patent Specification No. 35 26 565. The reaction mixture was stirred for 20 hours at ambient temperature, the dioxan was then evaporated off in a vacuum and the pH value was adjusted to 2.2 with trifluoroacetic acid. The conjugate of resorufin and peptide precipitated out. The precipitate was filtered off with suction and then reprecipitated by dissolving in 0.1M aqueous sodium hydrogen carbonate solution and acidification. By chromatography of the collected filtrates on Polygosil C18, there were obtained an additional 6.8 mg. of A-chain loop resorufin sarcosine.

TLC: (silica gel, elution agent as stated above) $R_f$: 0.56.

EXAMPLE 2

Obtaining monoclonal antibodies against human insulin

BALB/c mice (8 to 12 weeks old) were immunized intraperitoneally with 100 μg. human insulin adsorbed on aluminium hydroxide and *Bordetella pertussis* After 6 weeks, three further immunizations were carried out at 4 week intervals. There was thereby administered intraperitoneally, in each case, 50 pg. insulin adsorbed on aluminium hydroxide and *Bordetella pertussis.*

Fusion was carried out about 4 months after the last immunization. 4 days and 3 days before the fusioning, immunization was again carried out intraperitoneally and intravenously, respectively, with, in each case, 100 μg. insulin/phosphate buffered saline (PBS).

For the fusion, with reference to Galfré, Methods in Enzymology, 73, 3/1981, $10^8$ spleen cells of an immunized mouse were mixed with $2\times10^7$ myeloma cells (P3x63-Ag 8.653, ATCC-CRL 8375) and subsequently centrifuged for 10 minutes (300 g, 4° C.). The cells were again washed with balanced salt solution (BSS). The supernatant was removed. The cell sediment was mixed with 1 ml. of 60% PEG solution (M.W. 4000, Merck). Thereafter, 5 ml. RPMI 1640 medium (RPM=Rosewell Parker Memory Institute) without bovine fetal serum (FCS) were slowly added dropwise thereto and subsequently again 5 ml. RPMI 1640 medium with 10% FCS, then made up to 50 ml. with medium and centrifuged for 10 minutes at 400 g. The sedimented cells were taken up in RPMI 1640 medium with 10% FBS. $2\times10^5$ spleen cells were seeded into each of a 24 well cell culture plate (Nunc.). $1\times10^5$ spleen cells or $5\times10^4$ peritoneal exudate cells were added to each culture as feed cells. On the following day, hypoxanthine-azaserine selection medium (100 mM hypoxanthine and 1 pg./ml. azaserine) were added thereto.

After about 7 to 10 days, many clones were already visible. The supernatant of the primary cultures was tested by an ELISA process as described in Example 3. Primary cultures which contained antigen-specific antibodies were further cloned with the help of a fluorescence-activating cell sorter on 96 well cell culture plates (Nunc). As feed cells, there were used $1 \times 10^4$ peritoneal exudate cells or $2 \times 10^4$ spleen cells per 96 well culture.

In this way, exemplary hybridoma cell lines 2E6 (ECACC 88022502) and 3C4 (ECACC 88022501) were isolated.

For the production of ascites, $5 \times 10^6$ hybrid cells were injected intraperitoneally into mice which had been previously treated with 0.5 ml. pristane. 1 to weeks thereafter, ascites fluid could be obtained from the mice. The antibodies could be isolated therefrom in the usual way. These monoclonal antibodies are specifically directed against insulin and show no or only a little cross-reactivity with pro-insulin.

EXAMPLE 3

Screening test on antibodies against insulin

In order to be able to recognize the presence and specificity of antibodies against insulin in the serum of immunized mice or in the culture supernatant of the hybrid cells or in ascites, an ELISA process was used as test principle: microtiter plates were coated overnight at 37° C. with 1 pg. insulin/ml. of coating buffer (0.2M sodium carbonate/bicarbonate, pH 9.3 to 9.5). Followup treatment was then carried out with 0.9% aqueous sodium chloride solution and 1% albumin solution. Thereafter, washing was carried out with 0.9% aqueous sodium chloride solution. Subsequently, incubation was carried out at 37° C. for 1 hour with 100 μl. of sample and washing with 0.9% aqueous sodium chloride solution followed. This, in turn was followed by further incubation for 1 hour at 37° C. with 100 to 150 mU/ml. of a sheep-antimouse IgG-peroxidase conjugate. After a renewed washing step with 0.9% aqueous sodium chloride solution, the peroxidase activity was determined in the usual way (for example with ABTS, 30 minutes at ambient temperature, reading off of the extinction difference, ΔmE at 405 nm.).

The ELISA test can also be carried out as follows: The microtiter plates are first coated with a sheep anti-mouse-IgG (20 to 30 μg/ml. of coating buffer, from 1 hour up to overnight, 37° C.). Thereafter, further treatment is carried out as described above, the sample solution is added thereto and again washed. Finally, incubation is carried out with 250 mU/ml. of an insulin-peroxidase conjugate for 1 hour at 37° C. It is again washed and the peroxidase activity determined, for example, with ABTS.

The antibodies are additionally screened for the recognition of the insulin peptide as described in Example 4.

EXAMPLE 4

| Materials | |
|---|---|
| Microtitre plates | A: Nunc 4-42404 II |
| | B: Nunc 2-69620 |
| 12-canal pipette | Dynatech, Catalogue No. 77-887-00 |
| Plate shaker | Flow Laboratories, Titertek, catalogue No. 77-471-00 |

| Materials | -continued |
|---|---|
| Covering foil | Dynatech Plate Sealers, catalogue No. M 30. |
| ELISA reader | Dynatech MR 700 |
| Coating buffer | 50 mM sodium carbonate (pH 9.6) |
| Sampler buffer | 10 mM sodium phosphate (pH 7.4), 0.9% sodium chloride, 0.1% Tween 20, 1% Crotein C |
| Wash buffer | 0.9% sodium chloride, 0.1% Tween 20 |
| Antibody-enzyme conjugate | conjugate of peroxidase and the Fab fragment of a polyclonal antibody from sheep which is directed against the Fcγ part of mouse IgG, 113 mU/ml. in sample buffer |
| Substrate | 100 mMole/liter phosphate-citrate buffer (pH 4.4), 3.2 mMole/liter sodium perborate and 1.9 mMole/liter ABTS (diammonium salt of 2,2'-azino-di-(3-ethylbenzthiazoline-6-sulphonic acid) |
| Antibody | MAB against insulin 2E6 or 3C4 |
| Peptide derivative | A-chain loop (prepared according to Example 1), A-chain loop-resorufin-sarcosine (prepared according to Example 1) |
| Antigen | human insulin. |

In a preliminary experiment, there was determined the amount of antibody to be used in the actual specificity experiments.

For this purpose, microtiter plates were coated with insulin. Per 100 μl. cup, 2.5 μg. insulin per ml. of coating buffer were incubated for 1 hour at ambient temperature. Thereafter, the solution was sucked off and washing carried out three times with wash buffer.

Subsequently, dilution series of one of antibodies 2E6 and 3C4, using ascites, were prepared and added to the solid phase bound insulin. Dilutions were prepared using sample buffers from the fifth passage of the antibodies, at 1:100 concentration. In each case, incubation was carried out for 1 hour at ambient temperature, followed by subsequent washing.

The antibodies bound to insulin were determined by the addition of a conjugate of peroxidase and the Fab fragment of a polyclonal antibody from sheep which is directed against the Fcγ part of mouse IgG, via the reaction of the peroxidase with an added substrate. The detection reaction was started by the addition of the substrate to all of the cups. The measurement took place in an ELISA reader at 405 nm (reference wavelength 490 nm).

In the following experiments, "titer" is defined as the dilution of antibody at which half maximum binding took place. This amount of antibody was used in the following experiment.

The specificity of the monoclonal antibodies was investigated. For this purpose, the reactivities of individual antibodies were compared with various components present in solution.

In microtiter plates pre-coated with 1% crotein C, in each case there were pipetted in 50 μl. of a solution of the monoclonal antibody in double titer concentration and 50 μl. of antigen solution or solution of the peptide derivative (dilution series, see below), mixed and incubated for 30 minutes at ambient temperature. Thereafter, 100 μl. aliquots of the mixtures were transferred into microtiter plates coated with insulin.

| Dilution series | |
|---|---|
| human insulin | |
| A-chain loop | from 10 μg./ml. of sample buffer with sample buffer in the 5th stage |
| A-chain loop resorufin-sarcosine | |

In the following experiments, "molar relative affinity" is defined as the concentration, is moles/liter, of the substance to be determined which corresponds, i.e., reacts with, the titer of antibody as defined above.

The molar relative affinity of the MAB's 2E6 and 3C4 towards the unlabelled peptide from Example 1 was greater by a factor of 5 than towards human insulin, the molar relative affinity towards the resorufin-labelled peptide from Example 1 was greater by a factor of 1.8 than towards human insulin. It follows therefrom that, in each case, the peptide derivative is recognized somewhat more weakly than human insulin.

EXAMPLE 5

Insulin determination method by means of FPIA measurement

1935 μl. 0.1M potassium phosphate buffer (pH 7.8) were mixed with 20 μl. of sample, 20 μl. of ascites solution of the clone 2E6 ($6.4 \times 10^{-6}$ mole/liter IgG), as well as 25 μl. of a solution of the resorufin-labelled peptide from Example 1.

After incubation for 5 minutes at 37° C., the fluorescence polarization was measured (excitation wavelength: 575 nm; emission wavelength: 594 nm).

Fluorescence spectrometer F 4.000, Hitachi, with polarization measurement head.

The calibration curve so obtained is shown in the Figure of the accompanying drawing. Each measurement point corresponds to the average value from three individual measurements.

We claim:

1. Method for determining a protein using a homogeneous fluorescence polarization immunoassay comprising simultaneously incubating a sample solution with
   a) a peptide amino acid sequence labelled with a fluorescing compound, said sequence having from 6 to 14 amino acids, two of which must be cysteine residues, wherein said two cysteine residues form a disulphide bridge with one another, said amino acid sequence corresponding to an epitope of the protein to be determined, and
   b) an antibody which specifically binds to both said protein and to the peptide amino acid sequence, wherein said antibody has a molar relative affinity for the peptide amino acid sequence labelled with a fluorescing compound and a molar relative affinity for the protein to be determined, which affinities differ by no more than a factor of 6, and measuring depolarization of polarized light which has been passed through said sample solution as a determination of protein therein.

2. Method according to claim 1, wherein said peptide amino acid sequence is fluorescently labeled at an end of the sequence.

3. Method according to claim 1, wherein said antibody is an antibody which has been produced by immunizing a host animal with a sample of the protein to be determined.

4. Method according to claim 1, wherein said antibody is an antibody which has been produced by immunizing a host animal with a sample of the peptide amino acid sequence used in said immunoassay.

5. Method according to claim 1, wherein said antibody is a monoclonal antibody.

6. Method of claim 1, wherein said protein is human insulin.

7. Method of claim 1, wherein said peptide amino acid sequence corresponds to the a-chain loop amino acid sequence of human insulin.

8. Method of claim 1, wherein said fluorescing compound is resorufin or fluorescein.

* * * * *

UNITED STATES PATENT AND TRADEMARK OFFICE
CERTIFICATE OF CORRECTION

PATENT NO. : 5,070,025
DATED : December 3, 1991
INVENTOR(S) : Christian Klein et al.

It is certified that error appears in the above-identified patent and that said Letters Patent is hereby corrected as shown below:

Column 1, line 60: delete the first ".".

Column 2, line 49: change "be determined as ..." to -- be determined. As ... --.

Column 5, lines 50-53: change
"8. 3.95g Fmoc Cys (Trt)
these couplings were, in
9. 2.49g Fmoc Gln
each case, repeated once" to -- 8.  3.95 g. Fmoc Cys (Trt)  )
                               ) these couplings were, in
   9.  2.49 g. Fmoc Gln        )
                               ) each case, repeated here Column 7, line 2: change "1 pg/ml" to -- 1 ug/ml --.

Signed and Sealed this

Twenty-fifth Day of May, 1993

Attest:

MICHAEL K. KIRK

Attesting Officer    Acting Commissioner of Patents and Trademarks